(12) United States Patent
Agarwal et al.

(10) Patent No.: US 6,995,288 B2
(45) Date of Patent: Feb. 7, 2006

(54) APPARATUS AND METHOD FOR PRODUCTION OF METHANETHIOL

(75) Inventors: Pradeep K. Agarwal, deceased, late of Lancaster, CA (US); by Rehka Agarwal, legal representative, Lancaster, CA (US); Temi M. Linjewile, Lehi, UT (US); Ashley S. Hull, Bryan, TX (US); Zumao Chen, Midvale, UT (US)

(73) Assignee: University of Wyoming, Laramie, WY (US)

( * ) Notice: Subject to any disclaimer, the term of this patent is extended or adjusted under 35 U.S.C. 154(b) by 457 days.

(21) Appl. No.: 10/318,392

(22) Filed: Dec. 12, 2002

(65) Prior Publication Data

US 2004/0249217 A1    Dec. 9, 2004

Related U.S. Application Data

(63) Continuation of application No. PCT/US01/18984, filed on Jun. 13, 2001.
(60) Provisional application No. 60/211,317, filed on Jun. 14, 2000.

(51) Int. Cl.
*C07C 319/02*    (2006.01)

(52) U.S. Cl. .................. 568/70; 422/186; 422/186.04; 48/198.1

(58) Field of Classification Search .................. 568/70; 422/186, 186.04; 48/198
See application file for complete search history.

(56) References Cited

U.S. PATENT DOCUMENTS

| 5,609,736 A | | 3/1997 | Yamamoto |
| 5,711,147 A | | 1/1998 | Vogtlin et al. |
| 6,028,228 A | * | 2/2000 | Wachs .................. 568/482 |
| 6,066,901 A | | 5/2000 | Burkhart et al. |

OTHER PUBLICATIONS

Raulin et al., Formation of prebiochemical compounds in models of primitive Earth's atmosphere. Methane-hydrogen ulfide atmospheres, Origins Life (1975), 6(1-2), 91-97.*
Database Caplus on STN, Chemical abstracts (Columbus, Ohio, USA), CA:83:2987, RAULIN, F. et al, "Formation of prebiochemical compounds in models of primitive Earth's atmosphere. II. Methane-hydrogen sulfide atmospheres", Origins Life. 1975, 69, 6(1-2) pp. 91-97.

(Continued)

*Primary Examiner*—Johann Richter
*Assistant Examiner*—Chukwuma Nwaonicha
(74) *Attorney, Agent, or Firm*—Emery L. Tracy

(57) ABSTRACT

A method for the production of methyl mercaptan is provided. The method comprises providing raw feed gases consisting of methane and hydrogen sulfide, introducing the raw feed gases into a non-thermal pulsed plasma corona reactor, and reacting the raw feed gases within the non-thermal pulsed plasma corona reactor with the reaction $CH_4 + H_2S \rightarrow CH_3SH + H_2$. An apparatus for the production of methyl mercaptan using a non-thermal pulsed plasma corona reactor is also provided.

21 Claims, 1 Drawing Sheet

OTHER PUBLICATIONS

Database Caplus on STN, Chemical abstracts (Columbus, Ohio, USA), CA:132:209813, GORDON, C.L. et al, "Novel technique for the production of hydrogen using plasma reactors", Prepr. Symp.-Am. Chem. Soc., Div. Fuel Chem., 2000, 44(4) pp. 874-878, 2000.

Database Caplus on STN, Chemical abstracts (Columbus, Ohio, USA), CA:122:195579, ZAMAN, J., "Simulation of hydrogen separation from hydrogen sulfide decomposition gases using inorganic membranes", Gas Clean, High Temp., (Pap. Int. Symp.), 1993, 2$^{nd}$, pp. 671-686.

Database Caplus on STN, Chemical abstracts (Columbus, Ohio, USA), CA:120:33822, HELFRITCH, D.J., "Pulsed corona discharge for hydrogen sulfide decomposition", IEEE Trans. Ind. Appl. 1993, 29(5), pp. 882-886.P.S. McManus et al, *Damping in Cantilevered Traffic Signal Structures under Forced Vibration.*

Database Caplus on STN, Chemical abstracts (Columbus, Ohio, USA), CA;120:18174, KAWAHATA, M. et al, "Hydrocarbon reactions in corona discharge", Am. Chem. Soc. Div. Fuel. Chem. 1964, 8(2), pp. 33-41.

\* cited by examiner

APPARATUS AND METHOD FOR PRODUCTION OF METHANETHIOL

This application is a continuation of international application number PCT/01/18984, filed Jun. 13, 2001 (pending), which is a continuation of U.S. Provisional Patent application No. 60/211,317, filed Jun. 14, 2000. Priority is hereby claimed for both applications.

CONTRACTUAL ORIGIN OF INVENTION

This invention was made with U.S. Government support under Contract No. DE-FC02-91ER75680 awarded by the U.S. Department of Energy. The U.S. Government has certain rights in this invention.

BACKGROUND OF THE INVENTION

1. Field of the Invention

The present invention relates generally to the production of mercaptans (alkanethiols), accompanied by the simultaneous recovery of hydrogen, from feedstreams containing hydrogen sulfide and hydrocarbons (alkanes) and, more particularly, it relates to a process for the production of methanethiol (methyl mercaptan) in a corona reactor from a feedstream containing hydrogen sulfide and methane in which hydrogen is continuously recovered from the gaseous mixture of products and reactants through a membrane wall.

2. Description of the Prior Art

The principal impetus behind the synthesis of thiols comes from the production of synthetic rubber. Thiols permit control of viscosity during polymerization of the synthetic rubber. Alkanethiols have also found extensive use in other areas, such as in the area of agricultural chemicals. In particular, methyl mercaptan (methanethiol) is commonly used for the manufacture of methionine, an amino acid used in chicken feed. Methyl mercaptan is also used to produce dimethyl sulfide; this chemical minimizes deposition in steam crackers, and is also used to desulfurize refinery products. Other uses include intermediate for jet fuel additives and fungicides.

In the past, three principal processes have been described for the production of methyl mercaptan:

Reaction of Methyl Alcohol (Methanol) with Hydrogen Sulfide

Reaction of methyl alcohol with hydrogen sulfide is the principal method used commercially. The principal reaction is as follows:

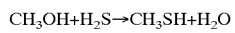

Several byproducts, including dimethyl sulfide, are also formed. The degree of methanol conversion increases with increase in temperature albeit at the cost of selectivity in favor of methyl mercaptan.

The catalysts in use today permit higher conversion and improved selectivity. The difference between various industrial processes lies primarily in the recipe of catalysts, operating temperature and pressure. The temperature generally lies in the range of two-hundred (200° C.) degrees Celsius to five-hundred (500° C.) degrees Celsius and the operating pressure ranges from one (atm) atmosphere to twenty-five (25 atm) atmosphere.

The principal disadvantage of this process, however, is that methanol is relatively expensive. In addition, product separation from reactants, and purification of methyl mercaptan requires fractionation. The presence of methanol changes the solubility of water in the organic phase. The fractionation to strip hydrogen sulfide from the effluent cannot be operated to obtain dry hydrogen sulfide as overhead, and dry methyl mercaptan as bottom product.

Reactions of Carbon Oxides with Hydrogen or Hydrogen Sulfide (in the Presence of Hydrogen)

The reactions of carbon oxides with hydrogen or hydrogen sulfide has been explored to reduce cost of raw materials such as methanol used in current commercial practice. The principal hydrogenation reactions, in the presence of sulfur, are as follows:

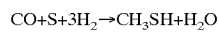

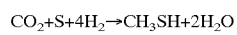

Alternatively, in the presence of hydrogen sulfide, the principal reactions are as follows:

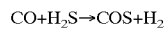

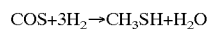

CO is the preferred reactant. Reactions involving $CO_2$ are comparatively much slower; in addition, larger amounts of hydrogen are required. The difference between various processes lies primarily in the combination of catalysts, operating temperature and pressure. The temperature generally lies in the range of two hundred and fifty (250° C.) degrees Celsius and four hundred (400° C.) degrees Celsius and the operating pressure, in excess of ten (10 atm) atmospheres, ranges preferably from thirty (30 atm) atmospheres to seventy (70 atm) atmospheres.

The principal disadvantage of this process is the requirement for hydrogen and/or carbon monoxide. Steam reforming of methane may be necessary to provide the raw materials. As noted earlier, use of carbon dioxide increases the hydrogen requirement. The principal byproducts include COS, $CS_2$, $CH_4$. Product separation from reactants remains an issue especially with reference to methane. Finally, the operating pressure is significantly higher than that required for synthesis of methyl mercaptan from methanol.

Hydrogenation of Carbonyl Sulfide or Carbon Disulfide

Methyl mercaptan can be produced through the hydrogenation of carbonyl sulfide according to the following:

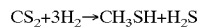

This catalytic reaction is carried out at temperatures between one hundred and fifty (150° C.) and three hundred and fifty (350° C.) degrees Celsius; the operating pressure is between ten (10 atm) atmospheres and fifty (50 atm) atmospheres. The major disadvantage of this process is the requirement for hydrogen as well as carbon disulfide. Production of hydrogen sulfide poses an additional problem even though its presence appears to assist the reaction. A variation on this approach, as follows:

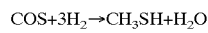

and avoids production of hydrogen sulfide. However, inexpensive sources of carbon disulfide and hydrogen remain elusive, but necessary.

SUMMARY

The present invention is a method for the production of methyl mercaptan. The method comprises providing raw feed gases consisting of methane and hydrogen sulfide, introducing the raw feed gases into a non-thermal pulsed plasma corona reactor, and reacting the raw feed gases within the non-thermal pulsed plasma corona reactor with the following reaction:

$$CH_4 + H_2S \rightarrow CH_3SH + H_2.$$

The present invention additionally includes an apparatus for the production of methyl mercaptan. The apparatus comprises raw feed gases consisting of methane and hydrogen sulfide and a non-thermal pulsed plasma corona reactor for reacting the raw feed gases within the non-thermal pulsed plasma corona reactor with the following reaction:

$$CH_4 + H_2S \rightarrow CH_3SH + H_2.$$

The present invention further includes a method for producing hydrogen from raw feed gases consisting of methane and hydrogen sulfide. The method comprises providing a non-thermal pulsed plasma corona reactor, introducing the raw feed gases into a non-thermal pulsed plasma corona reactor, and reacting the raw feed gases within the non-thermal pulsed plasma corona reactor with the reaction:

$$CH_4 + H_2S \rightarrow CH_3SH + H_2$$

to produce hydrogen.

DETAILED DESCRIPTION OF THE PREFERRED EMBODIMENTS

Figure 1:
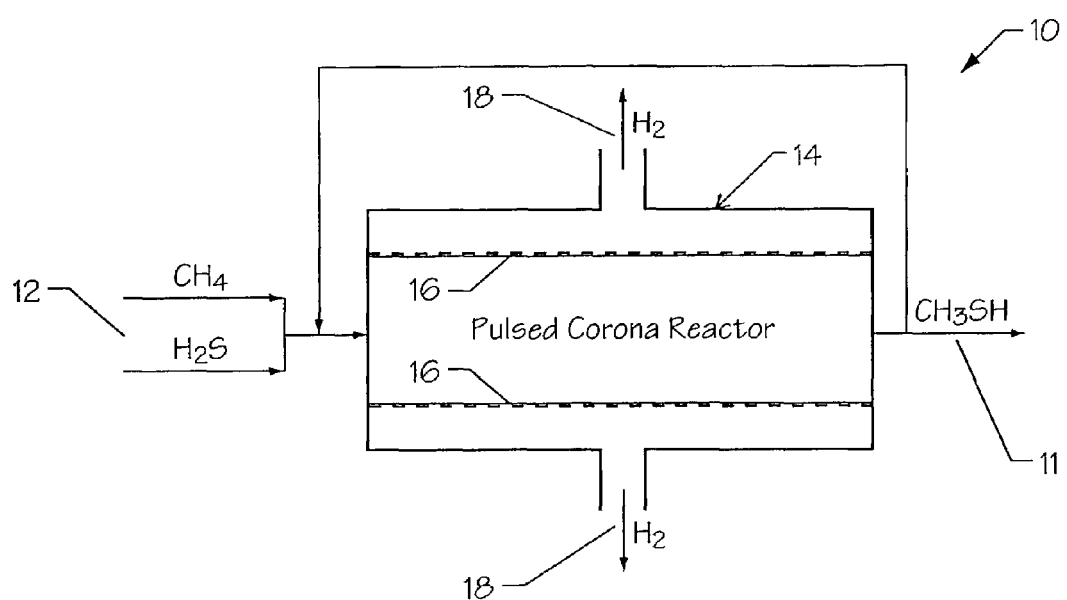
FIG. 1 is a schematic diagram illustrating the apparatus and method for the production of methyl mercaptan, constructed in accordance with the present invention.

As illustrated in FIG. 1, the present invention is an apparatus and method, indicated generally at 10, for the production of methyl mercaptan 11, using methane and hydrogen sulfide as raw feed gases 12, in a non-thermal pulsed plasma corona reactor 14. The raw feed gases 14 are available in sour natural gas streams and the production facility for producing the methyl mercaptan 11 can be sited, to advantage, near such gas fields. The principal overall reaction within the non-thermal pulsed plasma corona reactor 14 is as follows:

$$CH_4 + H_2S \rightarrow CH_3SH + H_2 \quad (A)$$

Within the non-thermal pulsed plasma corona reactor 14, conversion is expected to proceed through the dissociation of methane and hydrogen sulfide by energetic electrons according to the following:

$$CH_4 \rightarrow CH_3 + H \quad (B)$$

$$H_2S \rightarrow HS + H. \quad (C)$$

The recombination of the radical species leads to the following:

$$CH_3 + HS \rightarrow CH_3SH \quad (D)$$

$$H + H \rightarrow H_2. \quad (E)$$

High voltage pulses in the non-thermal pulsed plasma corona reactor 14 produce short-lived microdischarges that preferentially accelerate the electrons without imparting significant energy to the ions. The high voltage pulses within the non-thermal pulsed plasma corona reactor 14 is lowers power consumption. In addition, most of the energy applied goes to accelerating the electrons rather than the comparatively massive ions. Larger reactor volumes are consequently possible.

The non-thermal pulsed plasma corona reactor 14 has reactor walls 16 constructed from membrane materials—for example, palladium coated substrates, carbon among others—which permit selective permeation of hydrogen 18, Continuous removal of hydrogen 18 through the reactor walls 16 pushes reaction 4 towards completion.

A schematic diagram illustrating the apparatus and method of the present invention is shown in FIG. 1. It should be noted, however, that alternative arrangements devised to exploit the process concept more advantageously are within the scope of this invention.

The reaction and process described herein can also be viewed as a substitute for the Claus chemistry and operations used widely for sulfur recovery from streams containing hydrogen sulfide.

The advantages of the apparatus and process 10 of the present invention are clear:

The present invention permits the production of methyl mercaptan 11 from relatively inexpensive feedstock. Expensive preheating and pressurization of the feed gases 12 is also not required. The hydrogen 18 separation is relatively simple.

The present invention permits simultaneous production of hydrogen 18. The fuel value of methane is recovered in the form of cleaner-burning hydrogen. The hydrogen 14 can find use within the petroleum refinery if the process is used in conjunction with a desulfurization unit. Alternatively, hydrogen 14 can be used to generate clean electricity using fuel-cell technology.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

What is claimed is:

1. A method for the production of methyl mercaptan, the method comprising:
   providing raw feed gases consisting of methane and hydrogen sulfide;
   introducing the raw feed gases into a non-thermal pulsed plasma corona reactor; and
   reacting methane and hydrogen sulfide within the non-thermal pulsed plasma corona reactor to form methyl mercaptan and hydrogen.

2. The method of claim 1 wherein the raw feed gases are collected from sour natural gas streams.

3. The method of claim 1 wherein the reaction within the reactor proceeds through the dissociation of methane and hydrogen sulfide by energetic electrons to produce methyl radicals, HS radicals, and hydrogen radicals.

4. The method of claim 3 wherein the recombination of the radical species proceeds by methyl and JS radicals combining to form methyl mercaptan and hydrogen radicals combining to form hydrogen.

5. The method of claim 1 and further comprising:
high voltage pulses in the reactor, the high voltage pulses producing short-lived microdischarges that accelerate the electrons without imparting significant energy to the ions.

6. The method of claim 1 wherein the reactor walls are constructed from membrane materials, the membrane materials allowing selective permeation of hydrogen for continuous removal of hydrogen through the membrane materials.

7. The method of claim 6 wherein the membrane materials are palladium coated substrates.

8. An apparatus for the production of methyl mercaptan, the apparatus comprising:
raw feed gases consisting of methane and hydrogen sulfide; and
a non-thermal pulsed plasma corona reactor for reacting methane and hydrogen sulfide within the non-thermal pulsed plasma corona reactor to form methyl mercaptan and hydrogen.

9. The apparatus of claim 8 wherein the raw feed gases are collected from sour natural gas streams.

10. The apparatus of claim 8 wherein the reaction within the reactor proceeds through the dissociation of methane and hydrogen sulfide by energetic electrons to produce methyl radicals, HS radicals, and hydrogen radicals.

11. The apparatus of claim 10 wherein the recombination of the radical species proceeds by methyl and HS radicals combining to form methyl mercaptan and hydrogen radicals combining to form hydrogen.

12. The apparatus of claim 8 wherein the reactor includes high voltage pulses, the high voltage pulses producing short-lived microdischarges that accelerate the electrons without imparting significant energy to the ions.

13. The apparatus of claim 8 wherein the reactor walls are constructed from membrane materials, the membrane materials allowing selective permeation of hydrogen for continuous removal of hydrogen through the membrane materials.

14. The apparatus of claim 13 wherein the membrane materials are palladium coated substrates.

15. A method for producing hydrogen from raw feed gases consisting of methane and hydrogen sulfide, the method comprising:
providing a non-thermal pulsed plasma corona reactor;
introducing the raw feed gases into a non-thermal pulsed plasma corona reactor; and
reacting methane and hydrogen sulfide within the non-thermal pulsed plasma corona reactor to form methyl mercaptan and hydrogen.

16. The method of claim 15 wherein the raw feed gases are collected from sour natural gas streams.

17. The method of claim 15 wherein the reaction within the non-thermal pulsed plasma corona reactor proceeds through the dissociation of methane and hydrogen sulfide by energetic electrons to produce methyl radicals, HS radicals, and hydrogen radicals.

18. The method of claim 17 wherein the recombination of the radical species proceeds by methyl and HS radicals combining to form methyl mercaptan and hydrogen radicals combining to form hydrogen.

19. The method of claim 15 and further comprising:
high voltage pulses in the non-thermal pulsed plasma corona reactor, the high voltage pulses producing short-lived microdischarges that accelerate the electrons without imparting significant energy to the ions.

20. The method of claim 15 wherein the reactor walls are constructed from membrane materials, the membrane materials allowing selective permeation of hydrogen for continuous removal of hydrogen through the membrane materials.

21. The method of claim 20 wherein the membrane materials are palladium coated substrates.

* * * * *